(12) United States Patent
Sugita et al.

(10) Patent No.: US 11,899,013 B2
(45) Date of Patent: Feb. 13, 2024

(54) METHOD OF DETECTING OR QUANTIFYING DETECTION TARGET IN SPECIMEN, COMPOSITE PARTICLE, AND REAGENT

(71) Applicant: Canon Medical Systems Corporation, Otawara (JP)

(72) Inventors: Satoru Sugita, Nasushiobara (JP); Hirotoshi Tahara, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 572 days.

(21) Appl. No.: 16/910,148

(22) Filed: Jun. 24, 2020

(65) Prior Publication Data
US 2020/0408754 A1    Dec. 31, 2020

(30) Foreign Application Priority Data

Jun. 25, 2019  (JP) .................................. 2019-117556
Jun. 22, 2020  (JP) .................................. 2020-107149

(51) Int. Cl.
*G01N 33/551*     (2006.01)
*G01N 33/542*     (2006.01)
(Continued)

(52) U.S. Cl.
CPC ........... *G01N 33/551* (2013.01); *G01N 21/17* (2013.01); *G01N 21/75* (2013.01); *G01N 25/18* (2013.01); *G01N 25/482* (2013.01); *G01N 33/542* (2013.01); *G01N 33/54313* (2013.01); *G01N 23/2273* (2013.01); *G01N 33/538* (2013.01); *G01N 33/5375* (2013.01)

(58) Field of Classification Search
CPC . G01N 33/538; G01N 33/5375; G01N 33/553
USPC ................ 436/164, 524, 525, 528, 541, 805
See application file for complete search history.

(56) References Cited

U.S. PATENT DOCUMENTS 4,118,192 A       10/1978  Sawai et al.
10,060,913 B2 *   8/2018   Swager .................. G01N 21/59
(Continued)

FOREIGN PATENT DOCUMENTS

JP          58-11575 B2         3/1983
WO    WO-2011034678 A1 *      3/2011    ............. G01N 21/49

OTHER PUBLICATIONS

Jiang, H-R. et al., "Active Motion of a Janus Particle by Self-Thermophoresis in a Defocused Laser Beam," Physical Review Letters PRL, vol. 105, No. 268302, Dec. 31, 2010, 4 pages

*Primary Examiner* — Christopher L Chin
(74) *Attorney, Agent, or Firm* — Oblon, McClelland, Maier & Neustadt, L.L.P.

(57) ABSTRACT

According to one embodiment, a method of detecting or quantifying a detection target in a specimen includes: irradiating a reaction mixture containing composite particles and the specimen with light to promote binding between the composite particles and the detection target; and performing measurement on the reaction mixture irradiated with the light to detect or quantify the detection target. The composite particles each include a carrier particle including two or more regions having different physical properties on a surface, and an affinity substance carried on the carrier particle and having affinity to the detection target. The light can be absorbed by at least one of the two or more regions.

8 Claims, 3 Drawing Sheets

(51) Int. Cl.
- *G01N 33/543* (2006.01)
- *G01N 21/75* (2006.01)
- *G01N 21/17* (2006.01)
- *G01N 25/18* (2006.01)
- *G01N 25/48* (2006.01)
- G01N 23/2273 (2018.01)
- G01N 33/538 (2006.01)
- G01N 33/537 (2006.01)

(56) References Cited

U.S. PATENT DOCUMENTS

| | | | |
|---|---|---|---|
| 2019/0170736 A1* | 6/2019 | Swager | G01N 33/5432 |
| 2020/0166503 A1* | 5/2020 | Swager | G01N 21/55 |

* cited by examiner

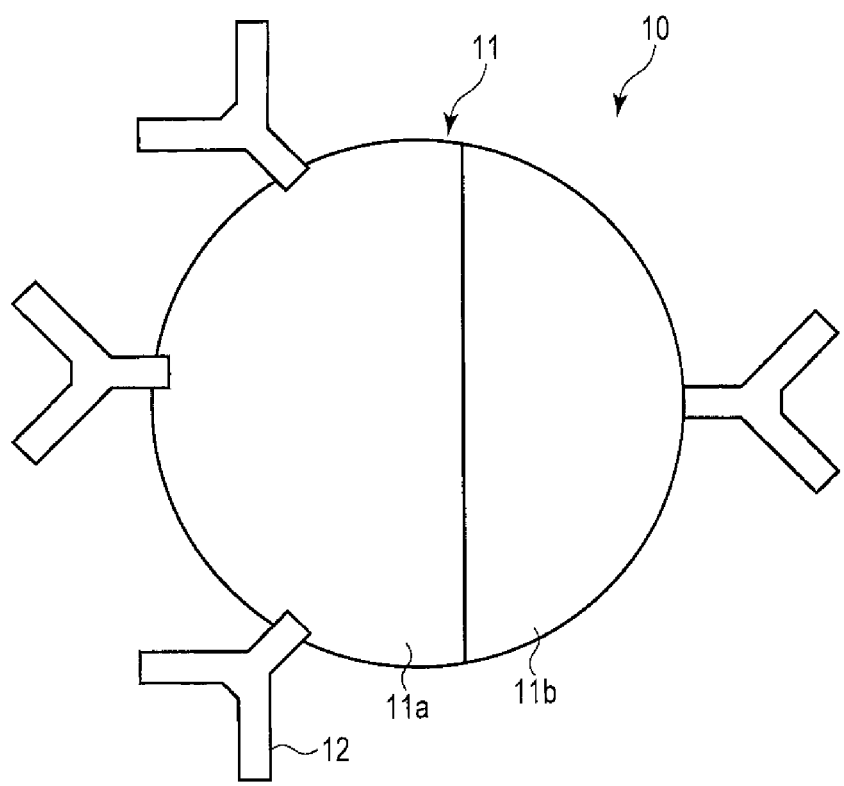
F I G. 1

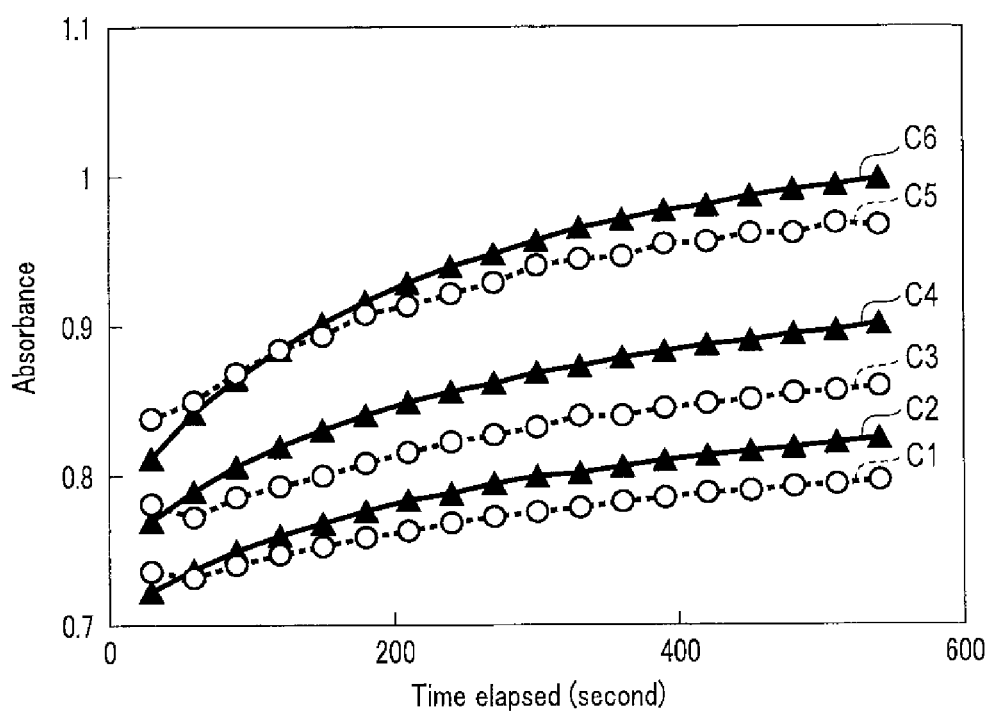
F I G. 3

METHOD OF DETECTING OR QUANTIFYING DETECTION TARGET IN SPECIMEN, COMPOSITE PARTICLE, AND REAGENT

CROSS-REFERENCE TO RELATED APPLICATIONS

This application is based upon and claims the benefit of priority from Japanese Patent Applications No. 2019-117556 filed Jun. 25, 2019 and No. 2020-107149 filed Jun. 22, 2020, the entire contents of which are incorporated herein by reference.

FIELD

Embodiments described herein relate generally to a method of detecting or quantifying a detection target in a specimen, a composite particle, and a reagent.

BACKGROUND

The latex agglutination method has been performed for detecting a detection target in a specimen. The latex agglutination method is a method in which, for example, for detecting an antigen in a specimen such as a biological sample, the specimen is mixed with latex that carries an antibody or a fragment thereof specifically bound to the antigen, and the degree of latex agglutination is measured, thereby detecting or quantifying the antigen.

According to this latex agglutination method, the antigen contained in the specimen cross-links multiple latex-bound antibodies, and promotes latex agglutination. However, cross-linking does not easily occur if the amount of antigen is small, and thus latex agglutination is not sufficient to detect the agglutinates. It has been therefore difficult to quickly detect a small amount of antigen.

On the other hand, it has been reported that when hemisphere surfaces of spherical silica particles or polystyrene particles are coated with gold to prepare asymmetric particles (also called Janus particles), these asymmetric particles, when put in water and irradiated with an infrared laser beam, make a propulsive motion with the gold-coated surfaces positioned at the back.

BRIEF DESCRIPTION OF THE DRAWINGS

FIG. 1 schematically shows an example of a composite particle;

FIG. 3 is a graph showing reaction curves.

DETAILED DESCRIPTION

Figure 2:
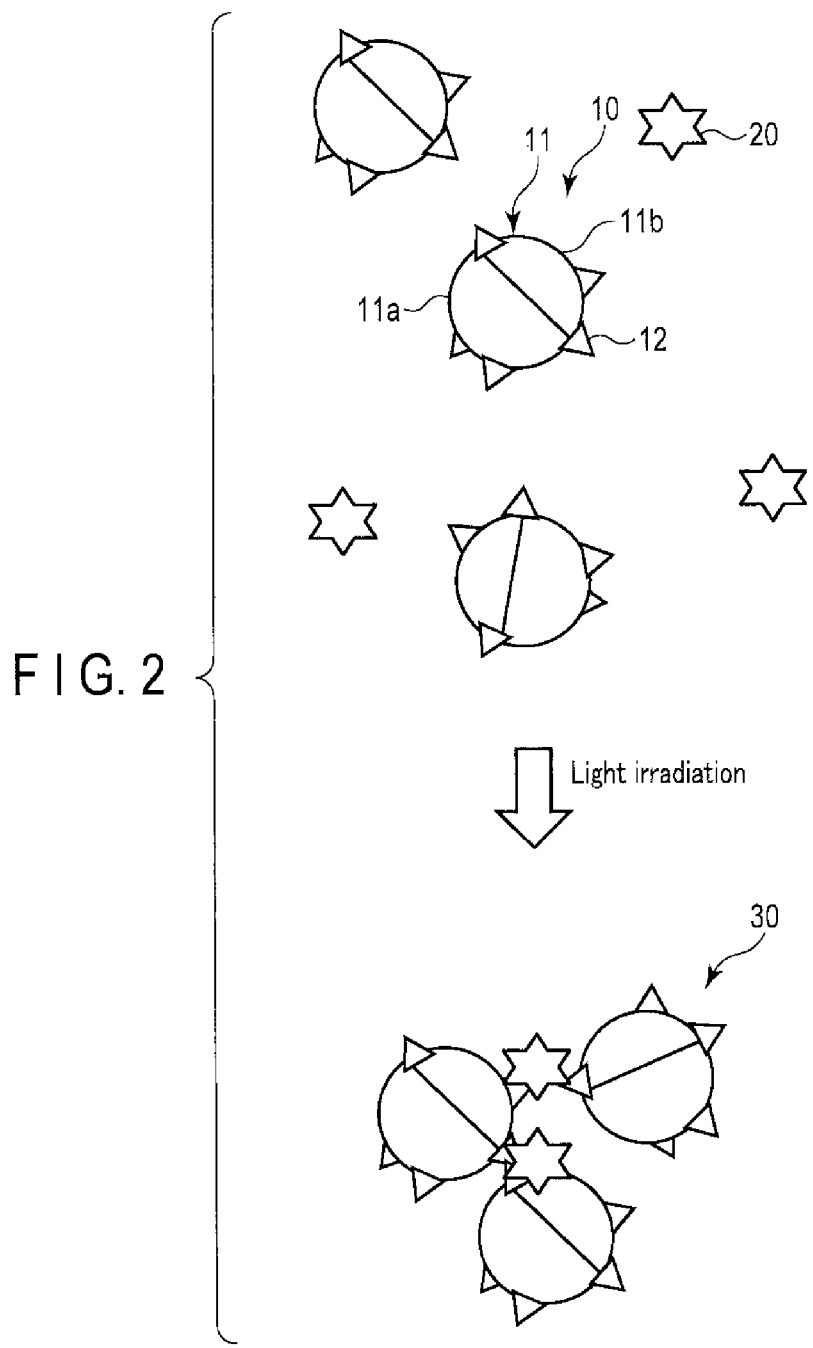
FIG. 2 schematically shows an example of a state in a reaction mixture.

1. Method of Detecting or Quantifying Detection Target in Specimen

According to one embodiment, a method of detecting or quantifying a detection target in a specimen includes:
 irradiating a reaction mixture with light,
  the reaction mixture containing:
   composite particles, each comprising a carrier particle including two or more regions having different physical properties on a surface, and an affinity substance carried on the carrier particle and having affinity to the detection target; and
   the specimen,
  the light being capable of being absorbed by at least one of the two or more regions,
 to promote binding between the composite particles and the detection target; and
 performing measurement on the reaction mixture irradiated with the light to detect or quantify the detection target.

This method uses principles of the latex agglutination method. That is, according to this method, if the detection target is present in the specimen, the carrier particles carrying the affinity substance are agglutinated by the reaction between the affinity substance and the detection target. By detecting or quantifying this agglutinate, the detection target can be detected or quantified. In this method, a particle including, on its surface, two or more regions having different physical properties is used as the carrier particle, and this particle is irradiated with light to cause a motion greater than the Brownian motion. This can promote the reaction between the affinity substance and the detection target.

1-1. Reaction Mixture

The reaction mixture contains the "specimen" and the "composite particle", which will be described below in this order.

"Specimen"

The specimen is a biological sample. For example, the specimen is a body fluid or an excrement extract, specific examples of which include blood, serum, plasma, urine, lymph fluid, sputum, and a feces extract.

The detection target in the specimen is a substance used for clinical diagnosis, specific examples of which include human immunoglobulin G, human immunoglobulin M, human immunoglobulin A, human immunoglobulin E, human albumin, human fibrinogen (fibrin and its degradation product), α-fetoprotein (AFP), C-reactive protein (CRP), myoglobin, a carcinoembryonic antigen, a hepatitis virus antigen, human chorionic gonadotropin (hCG), human placental lactogen (HPL), an HIV virus antigen, an allergen, a bacterial toxin, a bacterial antigen, an enzyme, a hormone (e.g., human thyroid stimulating hormone (TSH), and insulin), a nucleic acid, a nucleic acid amplified by PCR or the like, cytokine, and a drug, contained in body fluid, urine, sputum, feces, etc.

"Composite Particle"

The composite particle includes:
 a carrier particle including on its surface two or more regions having different physical properties; and
 an affinity substance carried on the carrier particle and having affinity to the detection target.

(Affinity Substance)

The affinity substance contained in the composite particle is preferably a substance specifically bound to the detection target. Specifically, the affinity substance may be a nucleic acid, protein, lipid, saccharide, or the like. The affinity substance may be an antigen or an antibody. If the detection target is an antigen, the affinity substance is an antibody. The antibody may be an immunoglobulin molecule of any type, and may be an immunoglobulin molecule fragment having an antigen binding site such as Fab. While the antibody may be a monoclonal antibody or a polyclonal antibody, a monoclonal antibody that recognizes a different antigenic determinant of an antigen is preferable. Alternatively, if the detection target is an antibody, the affinity substance may be an antigen having an antigenic determinant recognized by the antibody.

(Carrier Particle)

The carrier particle for carrying the affinity substance includes, on its surface, two or more regions having different physical properties. A particle including on its surface two or more regions having different physical properties is called an "asymmetric particle", "Janus particle", or "patch particle", and is publicly known.

The "two or more regions having different physical properties" may be, for example, two to five regions, preferably two to three regions, more preferably two regions. The number of "regions having different physical properties" described in this specification refers to the number of regions having different physical properties at adjacent regions.

When the carrier particle including on its surface two or more regions having different physical properties is irradiated with light, the difference in the amount of heat released at the two or more regions due to their different physical properties produces a local temperature gradient in a dispersion medium present around the carrier particle. As a result, the carrier particle is propelled from a higher-temperature dispersion medium side toward a lower-temperature dispersion medium side by the thermophoresis phenomenon.

When the carrier particle is caused to carry the affinity substance and the obtained composite particle is used in the latex agglutination method, the composite particle is able to exhibit the behavior similar to that of the carrier particle. That is, when the composite particle is irradiated with light, a local temperature gradient is produced in the dispersion medium present around the composite particle, and the composite particle makes a propulsive motion by the thermophoresis phenomenon. Consequently, the opportunities for the composite particle to come into contact with the detection target increase, and the binding reaction between the affinity substance and the detection target can be promoted.

Regarding the "two or more regions having different physical properties", if the difference in the physical properties is larger, the temperature gradient produced in the dispersion medium can be larger, and this can enhance the propulsion of the composite particle. Accordingly, the physical property is preferably a thermal conductivity.

That is, the carrier particle preferably includes on its surface two or more regions having different thermal conductivities. The difference in the thermal conductivities at the two or more regions is preferably 50 [W/m·K] or more, more preferably 100 [W/m·K] or more, still more preferably 150 [W/m·K], and even more preferably 200 [W/m·K]. The upper limit of the difference in the thermal conductivity at the two or more regions is, for example, but not particularly limited to, 500 [W/m·K]. In this specification, the thermal conductivity indicates a thermal conductivity at 20° C. If the carrier particle includes on its surface three or more regions having different physical properties, the "difference in the thermal conductivities" refers to a difference between a maximum value and a minimum value.

In a concrete embodiment, at least one of the two or more regions of the carrier particle is made of a metal or carbon, while the remainder of the two or more regions is made of a nonmetal.

In one embodiment, at least one of the two or more regions of the carrier particle is made of a metal, while the remainder of the two or more regions is made of a nonmetal. In this embodiment, for the metal and the nonmetal, any combination may be selected as long as physical properties are different from each other and a local temperature gradient can be produced in the dispersion medium present around the carrier particle. Examples of the metal include gold, silver, copper, iron, and alloy, and examples of the alloy include copper alloy such as brass, and nickel alloy. The nonmetal may be, for example, an inorganic substance or a polymer, specific examples of which include polystyrene, silica, and expanded polystyrene. In a preferred embodiment, at least one of the two or more regions of the carrier particle is made of gold, silver, copper, or iron, while the remainder of the two or more regions is made of a nonmetal.

In another embodiment, at least one of the two or more regions of the carrier particle is made of a carbon, while the remainder of the two or more regions is made of a nonmetal. In this embodiment, for the carbon and the nonmetal, any combination may be selected as long as the physical properties are different from each other and a local temperature gradient can be produced in the dispersion medium present around the carrier particle. The carbon is, for example, a nano-carbon material, specific examples of which include carbon nanotube, fullerene, and graphene. The nano-carbon material is known to have a high thermal conductivity. The nonmetal may be, for example, an inorganic substance or a polymer, specific examples of which include polystyrene, silica, and expanded polystyrene. A region made of the nonmetal may be a carbon allotrope having a different thermal conductivity from a carbon material of a region made of a carbon.

Typically, the two or more regions of the carrier particle are two regions. That is, the carrier particle typically includes on its surface two regions having different physical properties. More typically, the carrier particle includes on its surface two regions having different thermal conductivities.

If the carrier particle includes on its surface two regions having different physical properties, in a concrete embodiment, one of the two regions is made of a metal or carbon, while the other is made of a nonmetal. Here, "metal", "carbon" and "nonmetal" are as described above. In this embodiment, it is preferable that the region made of the metal or carbon have a surface area slightly smaller than that of the region made of the nonmetal. Specifically, if the entire surface area of the carrier particle is defined as 1, the surface area of the region made of the metal or carbon is preferably 0.35 to 0.45. If the surface area of the region made of the metal or carbon is slightly smaller than that of the region of the nonmetal, but not one half of the entire surface area of the carrier particle, the propulsion of the carrier particle can be enhanced.

The carrier particle may have any shape, for example, a spherical or rod shape, preferably a spherical shape. The spherical shape may be a true sphere or a spheroid. The rod shape may be a rod shape extending in a height direction, or a flat rod shape. The carrier particle has an average particle diameter of, for example, 20 to 800 nm, preferably 100 to 400 nm.

The "average particle diameter" of the carrier particle having any shape is defined as follows. A scanning electron microscope (SEM) is used to obtain an SEM image of carrier particles. Next, fifty particles in which the entirety of each of the particles is visible are selected randomly from the particles shown in each SEM image, and an area of each particle selected is obtained. Each diameter of a circle having an area equivalent to the obtained areas is calculated, and then an arithmetic average of these diameters is obtained. This arithmetic average (average equivalent circle diameter) is defined as the "average particle diameter".

As described above, a carrier particle including on its surface two or more regions having different physical properties is publicly known. Therefore, the carrier particle may be prepared according to a publicly-known technique. For example, the carrier particle may be prepared by coating part of a surface of a raw material particle with a material having a physical property differing from that of the raw material particle. The coating may be conducted by, for example, vapor deposition such as vacuum deposition. A coating thickness may be set to, for example, 20 to 30 nm.

For example, a carrier particle, including on its surface two regions composed of a region made of a nonmetal and a region made of a metal or carbon, can be prepared by using a spherical nonmetal particle as a raw material particle and subjecting a partial region of the nonmetal particle to metal or carbon coating. Alternatively, a carrier particle, including on its surface two regions composed of a region made of a metal or carbon and a region made of a nonmetal, may be prepared by using a spherical metal or carbon particle as a raw material particle and subjecting a partial region of the metal or carbon particle to nonmetal coating.

Here, for the "raw material particle", carrier particles generally used in an agglutination method can be used. Examples of the raw material particle include a cellulose particle, a porous glass particle, a silica gel particle, a low and high cross-linked polystyrene particle optionally cross-linked with divinylbenzene, a grafted copolymer particle, a polyacrylamide particle, a latex particle, a dimethylacrylamide particle optionally cross-linked with N,N-bis-acryloyl ethylene diamine, and a glass particle coated with a hydrophobic polymer. Alternatively, the raw material particle may be a particle containing alkanethiolate-induced gold, polyamide, acrylic copolymer, nylon, dextran, polyacrolein, etc.

The raw material particle is preferably a latex particle. The latex particle refers to a carrier particle used in the latex agglutination method. For the latex particle, those publicly known may be used, an example of which may be a polystyrene-based latex particle. Examples of the polystyrene-based latex particle may be a particle composed of a copolymer of styrene and glycidyl methacrylate.

(Concrete Example of Composite Particle)

FIG. 1 shows an example of a composite particle. A composite particle 10 shown in FIG. 1 is a composite particle used for detecting or quantifying an antigen in a specimen. The composite particle 10 includes:
 a spherical carrier particle 11 including, on its surface, a nonmetal region 11a and a metal region 11b; and
 an affinity substance (i.e., antibody) 12 carried on the carrier particle 11 and having affinity to a detection target (i.e., antigen).

In this example, "metal" and "nonmetal" are as described above. When the entire surface area of the carrier particle 11 is defined as 1, the metal region 11b has a surface area of, for example, 0.35 to 0.45. By setting the surface area of the metal region 11b to be slightly smaller than that of the nonmetal region 11a, the propulsion of the composite particle 10 can be enhanced.

When the composite particle shown in FIG. 1 is irradiated with light in the dispersion medium, the temperature of the dispersion medium present around the metal region 11b becomes higher than that of the dispersion medium present around the nonmetal region 11a, and therefore, a temperature gradient can be produced in an efficient manner in the dispersion medium present around the composite particle.

When the carrier particles shown in FIG. 1 are dispersed in the dispersion medium, the carrier particles may be attracted to each other and assemble on the metal region side. To avoid such self-assembly, the metal region of the carrier particle may be surface-modified with an organic polymer. The organic polymer is, for example, of hydrophobic nature, specific examples of which include polyethylene glycol and glycidyl methacrylate.

Needless to say, the composite particle is not limited to that shown in FIG. 1, and the carrier particle and the affinity substance may each take variations as described above. For example, with one region made of the same nonmetal as that constituting the region 11a being present in the metal region 11b shown in FIG. 1, the carrier particle may have three regions on the surface. Alternatively, with one region made of a second metal having a physical property different from a first metal constituting the region 11b being present in the metal region 11b shown in FIG. 1, the carrier particle may have three regions on the surface.

(Preparation of Composite Particle)

The composite particle can be prepared by causing the carrier particle to carry the affinity substance. Causing the carrier particle to carry the affinity substance is achieved by the same method of causing the latex particles to carry the affinity substance in the latex agglutination method. For example, if the affinity substance is an antibody or antigen, the carrier particle may be caused to carry the affinity substance using an ordinary method such as a physical adsorption method or a chemical binding method. Alternatively, the carrier particle may be caused to carry the affinity substance via substances having affinity to each other (e.g., avidin and biotin, or glutathione and glutathione S-transferase).

The affinity substance may be uniformly carried on the surface of the carrier particle, or selectively carried on a specified region of the carrier particle. Selective carrying of the affinity substance can be achieved by preliminarily binding a functional group to only a specified region of the carrier particle so as to carry the affinity substance via this functional group.

If the affinity substance is selectively carried, it is preferable that the region, on the front side toward which the carrier particle is propelled by light irradiation, carry the affinity substance. Specifically, it is preferable that a region having the lowest thermal conductivity carry the affinity substance. In the case of the composite particle 10 shown in FIG. 1, it is preferable that the nonmetal region 11a carry the affinity substance.

If the region on the front side in the propulsion direction of the carrier particle (nonmetal region 11a in FIG. 1) selectively carries the affinity substance, the following advantages can be provided.

As the region on the front side in the propulsion direction of the carrier particle carries the affinity substance, the opportunities to come into contact with the detection target increase, and the binding reaction of the affinity substance with the detection target can be promoted.

Furthermore, because the temperature of the region on the front side in the propulsion direction of the carrier particle does not become higher by light irradiation as compared to the region on the rear side in the propulsion direction of the carrier particle, if the region on the front side in the propulsion direction of the carrier particle selectively carries the affinity substance, thermal denaturation of the affinity substance can be prevented.

Moreover, when the region on the front side in the propulsion direction of the carrier particle selectively carries the affinity substance, because no affinity substance is present in the region on the rear side in the propulsion direction of the carrier particle, a temperature gradient can be efficiently produced in the dispersion medium without interfering with thermal conduction from the region on the rear side in the propulsion direction of the carrier particle to the dispersion medium.

"Reaction Mixture"

The reaction mixture may contain a buffer solution as a liquid component, in addition to the composite particle and the specimen. The total amount of the reaction mixture is not particularly limited, but may be, for example, 50 to 3000 μL, preferably 100 to 400 μL, if a small amount of detection target is detected or quantified.

The reaction mixture can be prepared by mixing, in a container, the buffer solution, the composite particle, and the specimen. For example, the reaction mixture may be prepared by mixing the buffer solution and the specimen, and adding the dispersion liquid of composite particles to the obtained intermediate mixture.

1-2. Light Irradiation

In this method, the reaction mixture is irradiated with light that can be absorbed by at least one of the two or more regions present on the surface of the carrier particle, to thereby promote the binding between the composite particle and the detection target.

Light is not particularly limited as long as it can be absorbed by at least one of the two or more regions present on the surface of the carrier particle. The light may be one that can be absorbed by the whole surface of the carrier particle. The light may be one having multiple wavelengths, but laser light is preferable. The light is preferably infrared light, more preferably infrared laser light. The light is, for example, Nd:YAG laser light (1064 nm).

The output of the laser is, for example, 20 to 50 mW. By changing the output of the laser, the propulsion speed of the composite particle can be controlled.

The light may be emitted continuously or intermittently by repetition of irradiation and non-irradiation. Even if either continuous light or pulse light is emitted, the propulsive motion of composite particles present in the reaction mixture can be caused. For pulse light, long-cycle pulse light that allows flashing to be recognized by the naked eye may be adopted.

The distance from the light source to the reaction container may be, for example, 5 mm. The material of the reaction container may be, for example, glass, polycarbonate, or polystyrene.

The entire reaction mixture may be irradiated with light. Alternatively, part of the reaction mixture may be irradiated with light as long as the propulsive motion of at least part of the composite particles present in the reaction mixture can be caused to cause a flow of a liquid part of the reaction mixture. The beam diameter of the laser light may be set to, for example, 1 to 3 mm with respect to approximately 7 mm of the width of the container wall surface perpendicular to the light traveling direction. A single portion of the reaction mixture may be irradiated with light using one light source, or a plurality of portions of the reaction mixture may be irradiated with light using a plurality of light sources.

The total light irradiation time for the reaction mixture is, for example, 2 to 60 minutes corresponding to the reaction time with the specimen.

The carrier particle itself is publicly known, and it is known that the movement of the carrier particle in the liquid can be controlled by the manner in which the carrier particle is irradiated with light because it has two or more regions having different physical properties on the surface. For example, it is known that the carrier particles can be dispersed or assembled in the liquid by the specific light irradiation manner. Therefore, according to publicly-known technique, the composite particles may be dispersed or assembled in the reaction mixture to control the movement of the composite particles, thereby increasing a reaction efficiency between the composite particle and the detection target.

FIG. 2 schematically shows an example of the state in the reaction mixture when irradiated with light. In FIG. 2, a detection target 20 is an antigen, and a composite particle 10 is the composite particle shown in FIG. 1, in which the composite particle 10 includes a carrier particle 11 and an antibody 12 carried on the carrier particle 11 and specifically bound to the detection target 20.

When the reaction mixture containing the detection target 20 and the composite particle 10 is irradiated with light, a local temperature gradient is produced in the dispersion medium (buffer solution of the reaction mixture) present around the composite particle 10. Specifically, because the metal region **11*b* has a higher thermal conductivity and easily releases the heat in comparison to the nonmetal region 11*a*, the temperature of the dispersion medium in the vicinity of the metal region 11*b* becomes higher than that of the dispersion medium in the vicinity of the nonmetal region 11*a*. Because of this temperature gradient, the composite particle 10 is propelled from the region 11*b* side toward the region 11*a*** side by the thermophoresis phenomenon.

Because of the propulsive motion of the composite particle 10, the binding reaction between the detection target 20 and the antibody 12 carried on the carrier particle 11 is promoted, and the agglutination reaction of the composite particle 10 is also promoted. Through the binding reaction between the composite particle 10 and the detection target 20 and the agglutination reaction, a complex (agglutinate) 30 is formed. When in the form of the complex (agglutinate) 30, the composite particle 10 cannot make a propulsive motion due to the complex's large mass.

1-3. Detection or Quantification

The detection target can be detected or quantified by determining a presence or absence of the complex (agglutinate) composed of the composite particle and the detection target.

The presence or absence of the complex can be determined by a visual observation or a turbidity measurement. The turbidity is calculated from, for example, an absorbance based on a transmitted light intensity measured by a photometer, or a scattered light quantity based on a scattered light intensity measured by a photometer. If the turbidity is high, the complexes agglutinate, suggesting that a detection substance is present. The wavelength of the light used may be set as appropriate so as to obtain a desired detection sensitivity according to the particle diameter, etc. of the carrier particle, etc. It is preferable that the light have a wavelength within a range from a near-ultraviolet light wavelength to a near-infrared wavelength (e.g., 340 to 800 nm) in which the conventional and general device can be used.

The visual observation or turbidity measurement may be performed intermittently at a given time point or continuously over time. In addition, the determination may be made based on the difference between the turbidity measurement value at a certain time point and the turbidity measurement value at another time point.

The "turbidity measurement" in the detecting or quantifying method includes not only direct measurement of the turbidity but also measurement of a parameter reflecting the turbidity. The parameter may be a difference among turbidity measurement values at multiple time points, an amount of the separated agglutinate, a turbidity of non-agglutinates after separation, etc.

Quantification of the detection target can be performed by measuring the turbidity based on the complex, and calculating the amount of the detection target in the specimen based on the correlation equation between the amount of the detection target and the turbidity.

The correlation equation between the amount of the detection target and the turbidity is prepared in advance. For the measurement of the amount of the detection target and the turbidity for creating the correlation equation, if there is more data, the reliability of the correlation equation increases. The data may be that related to two or more values for the amount of the detection target, preferably three or more values for the amount of the detection target.

The correlation equation between the amount of the detection target and the turbidity may not only be the equation indicating the direct correlation between the amount of the detection target and the turbidity but also the correlation equation between the amount of the detection target and the parameter reflecting the turbidity.

The amount of the detection target in the specimen can be calculated by substituting the turbidity measurement value for the correlation equation prepared.

1-4. Advantageous Effects

According to the method described above, because the composite particles make a propulsive motion, the opportunities to come into contact with the detection target increase, and the binding reaction between the affinity substance and the detection target can be promoted. Therefore, it is possible to quickly detect or quantify the detection target in the specimen.

Thus, according to the above-described method, the detection accuracy can be increased even if the amount of the detection target is very small. Moreover, the time required for binding, agglutination, etc. can be shortened. Furthermore, even if the reaction field is extremely narrow, the binding between the affinity substance and the detection target can be promoted, and therefore, the above-described method can be used not only for reaction in cells, wells, etc. as conventionally performed, but also for reaction in a microchemical process, a microchannel, a microreactor, etc.

Moreover, in the method described above, the composite particles make a propulsive motion through low-energy light irradiation, and this can increase the opportunities for the composite particles to come into contact with the detection target. In the above-described method, because the composite particles can make a propulsive motion through low-energy light irradiation, a cavitation (i.e., a physical phenomenon in which pressure difference in a liquid flow leads to the formation and collapse of bubbles in a short period of time) does not occur in an ambient environment of the composite particles, and as a result, it is possible to suppress damage to the specimen or decomposition of the reaction product.

1-5. Preferred Embodiment

The preferred embodiment of the above-described method is collectively shown below.

[1] A method of detecting or quantifying a detection target in a specimen, the method comprising:
irradiating a reaction mixture with light,
the reaction mixture containing:
composite particles, each comprising a carrier particle including two or more regions having different physical properties on a surface, and an affinity substance carried on the carrier particle and having affinity to the detection target; and
the specimen,
the light being capable of being absorbed by at least one of the two or more regions,
to promote binding between the composite particles and the detection target; and
performing measurement on the reaction mixture irradiated with the light to detect or quantify the detection target.

[2] The method according to [1], wherein the two or more regions have different thermal conductivities.

[3] The method according to [1] or [2], wherein at least one of the two or more regions is made of a metal or a carbon, and a remainder of the two or more regions is made of a nonmetal.

[4] The method according to [3], wherein the metal is gold, silver, copper, or iron.

[5] The method according to [3] or [4], wherein the nonmetal is an inorganic substance or a polymer.

[6] The method according to any one of [1] to [5], wherein the light is infrared light, preferably infrared laser light.

[7] The method according to any one of [1] to [6], wherein the affinity substance is an antigen or an antibody.

[8] The method according to any one of [1] to [7], wherein the two or more regions are two regions.

2. Composite particles and Reagent

According to another aspect, there is provided a composite particle for use in detecting or quantifying a detection target in a specimen, in which the composite particle includes:
a carrier particle including two or more regions having different physical properties on a surface; and
an affinity substance carried on the carrier particle and having affinity to the detection target.

For the composite particle, reference can be made to the description in the "Composite particle" section above. The composite particle can be used in the above-described method of detecting or quantifying a detection target in a specimen.

Furthermore, according to another aspect, there is provided a reagent for preparing a reaction mixture for detecting or quantifying a detection target in a specimen, in which the reagent includes:
dispersion particles, each of which is the above-described composite particle; and
a dispersion medium in which the dispersion particles are dispersed.

The dispersion medium is, for example, a buffer solution constituting the reaction mixture.

The reagent includes the composite particle described in the "Composite particle" section above, and the buffer solution constituting the reaction mixture. The reagent can be used for preparing a reaction mixture for detecting or quantifying a detection target in a specimen. Specifically, the reagent can be mixed with the specimen to prepare a reaction mixture.

EXAMPLES

The method of quantifying C-reactive protein (CRP) was performed in the following manner. In the present examples, the in-vitro diagnostic, CRP Auto "TBA" (Canon Medical Systems Corporation), available on the market as the C-reactive protein kit, was used.

Antibody-Bound Particles

In Example 1 (control), Reagent 2 (i.e., suspension of anti-human CRP polyclonal antibody-bound latex particle) included in the kit was used.

In Example 2, first, Janus particles were prepared as described below, and the obtained Janus particles were physically adsorbed to an anti-human CRP polyclonal antibody (anti-CRP polyAb) and post-coated with BSA, thereby preparing anti-human CRP polyclonal antibody-bound Janus particles. Example 2 used the suspension containing these particles at the same concentration as the particles of Example 1 (control).

Measurement Target

CRP standard solution "TBA" for latex (CRP concentration: 2 mg/dL, 4 mg/dL, 8 mg/dL)

1. Preparation of Janus Particles

[1-1. Preparation of Mother Particles 1]

Mixture 1 was prepared by weighing 2 g of styrene (St: KISHIDA CHEMICAL Co., Ltd.), 1.8 g of glycidyl methacrylate (GMA: Tokyo Chemical Industry Co., Ltd.), 0.04 g of divinylbenzene (DVB: KISHIDA CHEMICAL Co., Ltd.), and 110 g of ion-exchanged water, in a 300 ml four-necked flask.

The temperature of the mixture 1 was raised to 70° C. and then held at the same temperature, and nitrogen bubbling was performed at a flow rate of 50 ml/min to deoxidize the inside of the four-necked flask.

Solution 1 was prepared by weighing 0.06 g of V-50 (FUJIFILM Wako Pure Chemical Corporation) into 10 g of ion-exchanged water in a 30 ml eggplant-shaped flask.

The solution 1 was introduced into the deoxidized four-necked flask to prepare mixture 2 of the mixture 1 and solution 1. By stirring the mixture 2 at 200 rpm while kept at 70° C., soap-free emulsion polymerization was started.

Two hours after the start of polymerization, 0.3 g of GMA was introduced into the four-necked flask to prepare mixture 3. The mixture 3 was stirred for 22 hours at 200 rpm while kept at 70° C. to obtain dispersion liquid 1 of copolymer particles of St and GMA (hereinafter referred to as mother particles 1).

After the dispersion liquid 1 was centrifugally purified with ion-exchanged water, the final concentration was adjusted to 10.0 wt % to obtain dispersion liquid 2. The dispersion liquid 2 was stored in this state at 4° C. under light-shielding conditions.

When the particle size of the mother particle 1 in water was evaluated by the dynamic light scattering method, the weight average particle size was 200 nm.

[1-2. Preparation of Janus Particles]

[Step 1: Step of Forming Single-Layered Particle Film 1 of Mother Particles 1 on Silicon Wafer]

Silica particles having a weight average particle diameter of 5 nm and the mother particles 1 were co-dispersed in ion-exchanged water to prepare mixture 4 having a silica particle concentration of 1.84 vol % and a mother particle concentration of 4.50 vol %.

Through spin coating, the mixture 4 was applied onto a washed silicon wafer (washing conditions: ozone ashing at 120° C. for 10 minutes) to form a single-layered particle film 1 of mother particles on the silicon wafer. The spin coating conditions were as follows. After the mixture 4 was dropped on the silicon wafer, it was rotated at 1800 rpm for 30 seconds, and subsequently rotated at 2000 rpm for 30 seconds.

When the single-layered particle film 1 was observed with the scanning electron microscope (SEM), it was observed that part of the mother particles 1 was exposed from the silica particle matrix.

[Step 2: Step of modifying exposed part of single-layered particle film 1]

800 mg of mercaptosuccinic acid (FUJIFILM Wako Pure Chemical Corporation), 4.28 ml of 3-mercapto-1,2-propanediol (FUJIFILM Wako Pure Chemical Corporation), and 500 g of ion-exchanged water were weighed in a 2000 ml beaker, and a predetermined amount of triethylamine (KISHIDA CHEMICAL Co., Ltd.) was introduced to prepare solution 2 having pH 10.

The single-layered particle film 1 was immersed in the solution 2 and held for 18 hours in the state where the temperature was raised to 70° C. Thereby, the GMA-derived epoxy group in the exposed part of the mother particles 1 constituting the single-layered particle film layer 1 was chemically reacted (modified) with mercaptosuccinic acid, and 3-mercapto-1,2-propanediol to obtain single-layered particle film 2.

500 g of ion-exchanged water was weighed in a light-shielded 2000 ml beaker, the single-layered particle film 2 was immersed therein, and in this state, the single-layered particle film 2 was stored.

[Step 3: Step of Further Modifying Modified Part of Single-Layered Particle Film 2]

500 ml of iron (II) chloride aqueous solution was weighed in a 2000 ml beaker, and the single-layered particle film 2 was immersed therein and left in this state for 2 hours at room temperature. Thereby, iron ions were occluded in the modified part of the single-layered particle film 2 to obtain single-layered particle film 3.

An alkaline aqueous solution adjusted to pH 9 using a 0.1 NaOH aqueous solution was weighed in a 2000 ml beaker, and the single-layered particle film 3 washed with ion-exchanged water was immersed therein. Thereby, the occluded iron ions were chemically converted to magnetite to obtain single-layered particle film 4. The magnetite was coordinately bonded with the mercaptosuccinic acid-derived carboxyl group of the single-layered particle film 3 to have properties of oxide nanoparticles.

500 g of ion-exchanged water was weighed in a light-shielded 2000 ml beaker, the single-layered particle film 4 was immersed therein, and in this state, the single-layered particle film 4 was stored.

[Step 4: Step of Obtaining Mother Particles 2]

The single-layered particle film 4 was immersed in a hydrofluoric acid solution to remove the silica particle matrix to obtain single particle film 5. Further, the single-layered particle film 5 was immersed in ion-exchanged water and irradiated with ultrasonic waves for 30 minutes to separate and disperse the single-layered particle film 5 from the silicon wafer, thereby obtaining Mother particles 2.

The mother particles 2 were centrifugally purified with ion-exchanged water to obtain dispersion liquid 3. The dispersion liquid 3 was stored at 4° C. under light-shielding conditions.

By repeating Step 1 through Step 4, mother particles 2 in an amount necessary for Step 5 were secured.

[Step 5: Step of Obtaining Janus Particles]

Mixture 5 was prepared by weighing, in a 2 ml microtube, 2.5 wt % of a water dispersion liquid of mother particles 2, 0.03 g of ion-exchanged water, 0.4 mg of mercaptosuccinic acid (FUJIFILM Wako Pure Chemical Corporation), and 0.002 ml of 3-mercapto-1,2-propanediol (FUJIFILM Wako Pure Chemical Corporation).

After adding a predetermined amount of triethylamine (KISHIDA CHEMICAL Co., Ltd.) to the mixture 5 and adjusting to pH 10, the microtube was held while being shaken for 18 hours in an incubator at 70° C. Thereby, the GMA-derived residual epoxy group of the mother particles 2 was chemically reacted (modified) with mercaptosuccinic acid and 3-mercapto-1,2-propanediol to obtain Janus particles. The resulting Janus particles have on their surfaces a metal region of iron and a nonmetal region of a copolymer of styrene and glycidyl methacrylate.

After the Janus particles were centrifugally purified with ion-exchanged water, the final concentration was adjusted to 1.0 wt %, thereby obtaining dispersion liquid 4. The dispersion liquid 4 was stored in this state at 4° C. under light-shielding conditions.

2. Measurement of Absorbance

[2-1. Measuring Device]

Discrete clinical chemistry automatic analyzer TBA-120FR (Canon Medical Systems Corporation)

[2-2. Assay Parameter]

Sample (CRP standard solution of 2 mg/dL, 4 mg/dL or 8 mg/dL); 3.0 µL

Reagent 1 (buffer solution); 150 µL

Reagent 2 (suspension of anti-human CRP polyclonal antibody-bound latex particles, or suspension of anti-human CRP polyclonal antibody-bound Janus particles); 150 µL Photometric wavelength (572 nm) response curve acquired

[2-3. Test Protocol]

Example 1 (Latex Particles and Piezo Agitation)

The Sample (any one of CRP standard solution of 2 mg/dL, CRP standard solution of 4 mg/dL, or CRP standard solution of 8 mg/dL) was dispensed by the sample dispensing probe into the reaction container (glass tube). Reagent 1 (buffer solution, hereinafter, R1) was dispensed by the first-reagent dispensing probe into the reaction container into which the Sample was dispensed, and stirred with the piezo stirrer provided in the stirring unit. After a predetermined time from the agitation by the stirring unit elapsed, Reagent 2 (suspension of anti-human CRP polyclonal antibody-bound latex particles, hereinafter, R2) was dispensed by the second-reagent dispensing probe into the reaction container containing the intermediate mixture of the Sample and R1, and stirred with the stirrer unit.

After the agitation by the stirrer unit, the reaction container containing the reaction mixture of the Sample, R1, and R2 was irradiated with the light from the light source provided in the photometry unit, and the light passing through the reaction container was detected by the photodetector. The detection was conducted every 30 seconds for 9 minutes. The absorbance was calculated based on the intensity of the transmitted light detected, and the amount of change with respect to the absorbance at the detection start time was calculated.

The results are shown in FIG. 3. In FIG. 3, curve C1 shows the result when the CRP standard solution of 2 mg/dL was used, curve C3 shows the result when the CRP standard solution of 4 mg/dL was used, and curve C5 shows the result when the CRP standard solution of 8 mg/dL was used.

Example 2 (Janus Particles and Light Irradiation)

The Sample (any one of CRP standard solution of 2 mg/dL, CRP standard solution of 4 mg/dL, or CRP standard solution of 8 mg/dL) was dispensed by the sample dispensing probe into the reaction container (glass tube). Reagent 1 (buffer solution, hereinafter, R1) was dispensed by the first-reagent dispensing probe into the reaction container into which the Sample was dispensed, and the resulting intermediate mixture was not stirred with the stirring unit. After a predetermined time from the dispensing of R1 elapsed, Reagent 2 (suspension of anti-human CRP polyclonal antibody-bound Janus particles, hereinafter, R2) was dispensed by the second-reagent dispensing probe into the reaction container containing the intermediate, mixture, and the resulting reaction mixture was not stirred by the stirring unit. Instead, the area below the photometric point of the reaction container was irradiated for 9 minutes with the pulsed laser light (YAG laser, pulse energy: 50 to 400 mJ, wavelength: 1064 nm, beam diameter: 2 mm, distance from the light source to the reaction container: 5 mm).

The reaction container containing the reaction mixture of the Sample, R1 and R2 was irradiated with the light from the light source provided in the photometry unit, and the light passing through the reaction container was detected by the photodetector. The detection was conducted every 30 seconds over the irradiation period of the pulsed laser light (9 minutes). However, the irradiation with the pulsed laser light was stopped at the time of detection. The absorbance was calculated based on the intensity of the transmitted light detected, and the amount of change with respect to the absorbance at the detection start time was calculated.

The results are shown in FIG. 3. In FIG. 3, curve C2 shows the result when the CRP standard solution of 2 mg/dL was used, curve C4 shows the result when the CRP standard solution of 4 mg/dL was used, and curve CE shows the result when the CRP standard solution of 8 mg/dL was used.

[2-4. Results]

As shown in FIG. 3, in any of the cases in which the CRP concentration was 2 mg/dL, 4 mg/dL and 8 mg/dL, when the Janus particles were used as the carrier particles and light irradiation was performed, an apparent reaction promotion effect was confirmed in comparison to when the latex particles were used as the carrier particles and piezo agitation was performed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A method of detecting or quantifying a detection target in a specimen, the method comprising:

irradiating a reaction mixture with infrared pulse laser light, the reaction mixture containing: (1) composite particles, each comprising a carrier particle including two regions including a first region made of a metal and a second region made of a nonmetal on a surface, and an affinity substance carried on the carrier particle and having affinity to the detection target, and (2) the specimen, the infrared pulse laser light being capable of being absorbed by the first region, to promote binding between the composite particles and the detection target; and irradiating the reaction mixture with a measurement light after the irradiation with the infrared pulse laser light, and measuring a transmitted light intensity or a scattered light intensity to detect or quantify the detection target based on a result of the measurement, wherein the irradiation with the infrared pulse laser light is stopped during the irradiation with the measurement light.

2. The method according to claim 1, wherein the metal is gold, silver, copper, or iron.

3. The method according to claim 1, wherein the nonmetal is an inorganic substance or a polymer.

4. The method according to claim 1, wherein the affinity substance is an antigen or an antibody.

5. The method according to claim 1, wherein the affinity substance is selectively carried on the second region of the carrier particle.

6. The method according to claim 1, wherein the first region has a surface area of 0.35 to 0.45, when the entire surface area of the carrier particle is defined as 1.

7. The method according to claim 1, wherein the measurement light has a wavelength within a range of 340 to 800 nm.

8. The method according to claim 1, wherein the carrier particle has an average particle diameter of 20 to 800 nm.

* * * * *